(12) United States Patent
Palo et al.

(10) Patent No.: US 11,501,420 B2
(45) Date of Patent: Nov. 15, 2022

(54) RECONSTRUCTING PHASE IMAGES WITH DEEP LEARNING

(71) Applicants: PerkinElmer Cellular Technologies Germany GmbH, Hamburg (DE); PerkinElmer Health Sciences Canada, Inc., Woodbridge (CA)

(72) Inventors: Kaupo Palo, Talinn (EE); Abdulrahman Alhaimi, Woodbridge (CA)

(73) Assignees: PerkinElmer Cellular Technologies Germany GmbH, Hamburg (DE); PerkinElmer Health Sciences Canada, Inc., Woodbridge (CA)

( * ) Notice: Subject to any disclaimer, the term of this patent is extended or adjusted under 35 U.S.C. 154(b) by 147 days.

(21) Appl. No.: 17/028,448

(22) Filed: Sep. 22, 2020

(65) Prior Publication Data

US 2021/0097661 A1   Apr. 1, 2021

Related U.S. Application Data

(60) Provisional application No. 62/906,605, filed on Sep. 26, 2019.

(51) Int. Cl.
*G06T 5/50*     (2006.01)
*G06N 20/00*    (2019.01)
(Continued)

(52) U.S. Cl.
CPC ........... *G06T 5/50* (2013.01); *G01N 33/4833* (2013.01); *G06N 3/08* (2013.01); *G06N 20/00* (2019.01);
(Continued)

(58) Field of Classification Search
CPC . G06T 5/50; G06T 5/002; G06T 2207/10056; G06T 2207/20081;
(Continued)

(56) References Cited

U.S. PATENT DOCUMENTS 10,176,565 B2 *  1/2019  Greenfield ............. G02B 21/16
11,209,737 B1 * 12/2021  Stoschus ................ G06V 10/14
(Continued)

FOREIGN PATENT DOCUMENTS

WO        00/26622 A1   5/2000
WO     2005/073689 A1   8/2005
WO     2005/083377 A1   9/2005

OTHER PUBLICATIONS

Yichen Wu et al: "Cross-modality deep learning brings bright-field microscopy contrast to holography", arxiv.org, Cornell University Library, 201 Olin Library Cornell University Ithaca, NY 14853, Nov. 17, 2018 (Nov. 17, 2018), XP081144239, DOI: 10.1038/S41377-019-0139-9.

(Continued)

*Primary Examiner* — Lewis G West
(74) *Attorney, Agent, or Firm* — Banner & Witcoff, Ltd.

(57) ABSTRACT

Aspects relate to reconstructing phase images from brightfield images at multiple focal planes using machine learning techniques. A machine learning model may be trained using a training data set comprised of matched sets of images, each matched set of images comprising a plurality of brightfield images at different focal planes and, optionally, a corresponding ground truth phase image. An initial training data set may include images selected based on image views of a specimen that are substantially free of undesired visual artifacts such as dust. The brightfield images of the training data set can then be modified based on simulating at least one visual artifact, generating an enhanced training data set for use in training the model. Output of the machine learning (Continued)

model may be compared to the ground truth phase images to train the model. The trained model may be used to generate phase images from input data sets.

20 Claims, 12 Drawing Sheets

(51) Int. Cl.
*G01N 33/483* (2006.01)
*G06N 3/08* (2006.01)
*G06T 5/00* (2006.01)

(52) U.S. Cl.
CPC .... *G06T 5/002* (2013.01); *G06T 2207/10056* (2013.01); *G06T 2207/20081* (2013.01); *G06T 2207/30072* (2013.01)

(58) Field of Classification Search
CPC . G06T 2207/30072; G06T 2207/20084; G06T 11/00; G01N 33/4833; G06N 3/08; G06N 20/00; G06N 3/0454; G06N 3/088
See application file for complete search history.

(56) References Cited

U.S. PATENT DOCUMENTS

| | | | | |
|---|---|---|---|---|
| 2005/0057756 | A1* | 3/2005 | Fang-Yen | G01B 9/02057 356/497 |
| 2005/0105097 | A1* | 5/2005 | Fang-Yen | G01B 9/02057 356/497 |
| 2015/0331228 | A1* | 11/2015 | Horstmeyer | G02B 21/361 348/79 |
| 2018/0173839 | A1* | 6/2018 | Fang | G06T 7/001 |
| 2019/0020530 | A1* | 1/2019 | Au | H04L 27/362 |
| 2020/0034999 | A1* | 1/2020 | Van Heteren | A61B 6/541 |
| 2020/0250822 | A1* | 8/2020 | Jackson | G06T 7/0014 |
| 2021/0073513 | A1* | 3/2021 | Porto | G06V 20/693 |
| 2021/0089750 | A1* | 3/2021 | Jackson | G06T 7/70 |
| 2021/0097661 | A1* | 4/2021 | Palo | G01N 33/4833 |
| 2021/0158521 | A1* | 5/2021 | Shaked | G06T 7/13 |
| 2021/0264214 | A1* | 8/2021 | Ozcan | G06V 20/698 |
| 2021/0327080 | A1* | 10/2021 | Jackson | G06T 7/529 |
| 2022/0147770 | A1* | 5/2022 | Jain | G06K 9/6262 |
| 2022/0203370 | A1* | 6/2022 | Choi | B01L 3/502784 |

OTHER PUBLICATIONS

Connor Shorten et al: "A survey on Image Data Augmentation for Deep Learning", Journal of Big Data, vol. 6, No. 1, Jul. 6, 2019 (Jul. 6, 2019), XP055738703, DOI: 10.1186/s40537-019-0197-0, abstract, pp. 1-5.
Yair Rivenson et al: "Deep learning in holography and coherent imaging", Light: Science & Applications, vol. 8, No. 1, Sep. 11, 2019 (Sep. 11, 2019), XP055723773, DOI: 10.1038/s41377-019-0196-0.
Jan. 13, 2021—ISR & WO—PCT/IB2020/058915.
E.D. Barone-Nugent, A. Barty, and K.A. Nugent, "Quantitative phase-amplitude microscopy I: optical microscopy", Journal of Microscopy, vol. 206, Pt 3 Jun. 2002, pp. 194-203.
Rivenson, Y., Zhang, Y., Günaydin, H. et al. Phase recovery and holographic image reconstruction using deep learning in neural networks. Light Sci Appl 7, 17141, Feb. 2018, pp. 1-9.
Falk, T., Mai, D., Bensch, R. et al. U-Net: deep learning for cell counting, detection, and morphometry. Nat Methods, Jan. 2019, pp. 1-10.
European Patent Application No. 20786599.9.

\* cited by examiner

RECONSTRUCTING PHASE IMAGES WITH DEEP LEARNING

CROSS-REFERENCE TO RELATED APPLICATION

This application claims priority to U.S. Provisional Patent Application No. 62/906,605 filed on Sep. 26, 2019, titled "Reconstructing Phase Images with Deep Learning," the contents of which are expressly incorporated herein by reference in their entirety.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD

This disclosure relates generally to apparatus, methods, and systems for reconstructing phase images from image sets, including those from brightfield microscopic images, using machine learning techniques.

BACKGROUND

Microscopy has enabled us to see parts of our world at levels of detail not visible to the human eye. Technological advancements have progressed far beyond the "looking glass" approach of old, and modern techniques are able to provide increasingly clear images of the microscopic world. Imaging techniques look to both bring a high level of zoom resolution to observe samples as well as to isolate subject elements of interest. These techniques may be particularly interesting in the study of biological cells.

Quantitative phase imaging is one such technique. Brightfield imaging techniques may illuminate a sample and collect the light passing through a sample for viewing by a user. Due to the nature of optical refraction through the different elements included in the sample, a pair of brightfield images at different focal planes of a sample may be processed and combined to reconstruct a clear image of the sampled subject, such as cells included in sample on a plate for use in the microscope.

Simple brightfield imaging can be greatly enhanced through use of phase imaging. For example, a view of a specimen (e.g., a microscope or other specimen view to be imaged) may be imaged at two or more different focal planes to provide two or more brightfield images, then contrasts in refraction indexes may be used to generate a combined, enhanced phase image. For example, in a specimen having a sample containing cells in water, the known refraction index of water (n=1.33) may be used to isolate and identify the cells (n=1.35-1.38, for example) and produce a phase image focused on the cells in the sample. The brightfield images may be processed and combined based on the fundamental phase equation which is a special form of transport of intensity equation for paraxial illumination (M. R. Teague, "Deterministic phase retrieval: a Green's function solution," Journal of the Optical Society of America, vol. 73, no. 11, pp. 1434-1441, 1983):

$$\nabla/\nabla\Phi + I\Delta\Phi = -\partial_z I$$

where I is light intensity as a function over space coordinates x, y and z, $\Phi$ is phase of the light wave as a function of space coordinates, $\nabla$ and $\Delta$ are correspondingly gradient operator and Laplace operator in xy-plane, and $\partial_z I$ is derivative of intensity along z axis. Additional information about brightfield phase imaging may be found in the paper "Quantitative phase-amplitude microscopy I: optical microscopy" by E. D. Barone-Nugent et al., Journal of Microscopy, Vol. 206, Pt. 3 Jun. 2002, pp. 193-203.

Brightfield phase imaging can be a powerful tool. While it works well in some use-cases, this approach may not perform well when faced with common artifacts (e.g., dust particles, water droplets, well edges/borders), and may take substantial time (i.e., 3-5 seconds) to generate one phase image. Disturbances in the optical path (e.g., visual artifacts, or merely "artifacts") may present a particular problem in phase images, since they do not refract light but absorb it. These disturbances or artifacts can lead to undesirable results in a generated phase image, since the phase equation does not capture the absorption effects and accounting for those effects is an ill posed problem and is computationally expensive. Without proper accounting of absorption, the phase solution will be severely and nonlocally distorted.

Another shortcoming of brightfield phase imaging is boundary regions of images. For example, because there is no useful data beyond image edges, computed phase images will include blurring at boundary regions representing edges of the image. In another example, the well boundaries of a sample well plate may lead to similar issues, as part of the light is fully absorbed within the imaged area. Other problems include illumination inhomogeneities combined with incompletely paraxial illumination that produces a significant background component. Sufficient background removal may also deteriorate the signal.

Aspects described herein may address these and other shortcomings using a novel machine learning model that is trained based on training data sets and simulated visual artifacts. Through the novel techniques described herein, improved phase images may be generated from sets of brightfield images. This may improve the abilities of scientists and researchers to, for example, view the structure of cell samples through enhanced image clarity and isolation of the cells relative to background content.

SUMMARY

Described herein are techniques incorporating artificial intelligence and machine learning to leverage deep learning algorithms to automatically reconstruct high quality phase images which may reduce the impact of artifacts and imaging quality problems identified herein. These techniques may also generate a phase image in less time than prior techniques (e.g., less than 1 second compared to prior techniques taking multiple seconds).

Aspects discussed herein relate to reconstructing phase images from brightfield images at multiple focal planes using machine learning techniques. A machine learning model may be trained to generate phase images based on sets of brightfield images. In the example of imaging a specimen that comprises a view of a sample well plate that further comprises one or more sample (micro)wells, training data sets may be selected based on those sample well plate views and/or images that avoid visual artifacts such as the sample well plate borders, the (micro)well borders, and/or other visual artifacts such as dust. The machine learning model may be trained to reduce the impact of visual artifacts on the resulting phase image by considering a sub-region within the overall specimen and/or sample contained therein. The training data set may be enhanced by creating copies of images in the training data set and adding simulated visual artifacts to create simulated training data set images. In a supervised training approach, the machine learning model may be trained using the simulated training data set images, and the machine learning model may learn to adapt output based on the simulated visual artifacts.

Matched image sets in the data set may be used as input to the machine learning model during training, where each matched image set may comprise two or more brightfield images corresponding to views of a specimen, each at a different focal plane, and a ground truth phase image of the specimen generated based on the corresponding two or more brightfield images. Generated output of the machine learning model based on the matched image sets may be compared against corresponding ground truth phase images to train the model. Additionally and/or alternatively, an unsupervised training approach may be taken using a training data set that does not need to have corresponding ground truth images, where generated output of the machine learning model is evaluated using a phase equation. The trained model may be used to generate phase images from input data sets of brightfield image pairs.

Corresponding methods, apparatus, systems, and computer-readable media are also within the scope of the disclosure.

These features, along with many others, are discussed in greater detail below.

BRIEF DESCRIPTION OF THE FIGURES

The present disclosure is illustrated by way of example and not limited in the accompanying figures in which like reference numerals indicate similar elements and in which.

DETAILED DESCRIPTION

Figure 1:
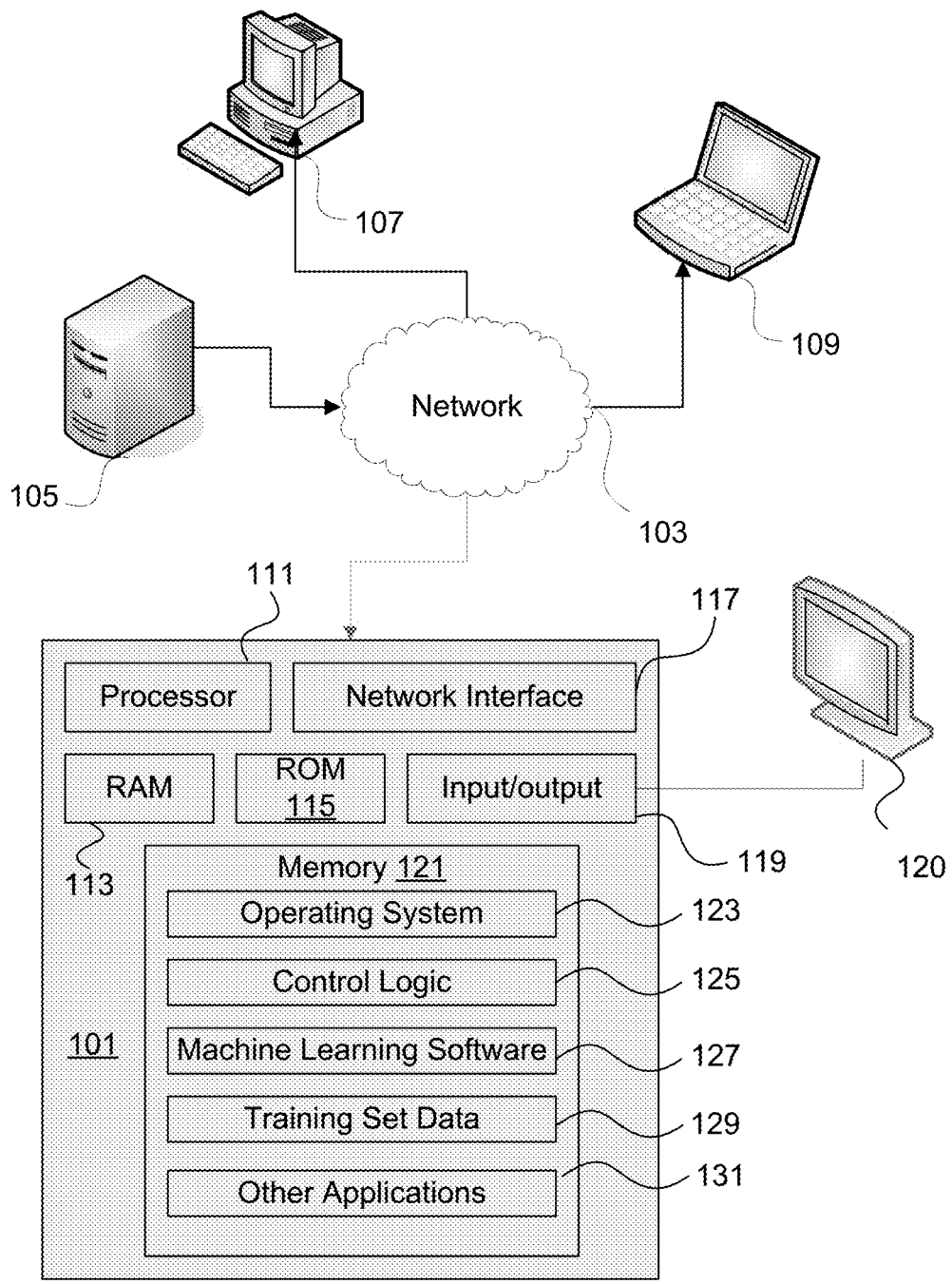
FIG. 1 depicts an example of a computing device that may be used in implementing one or more aspects of the disclosure in accordance with one or more illustrative aspects discussed herein.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope of the present disclosure. Aspects of the disclosure are capable of other embodiments and of being practiced or being carried out in various ways. Also, it is to be understood that the phraseology and terminology used herein are for the purpose of description and should not be regarded as limiting. Rather, the phrases and terms used herein are to be given their broadest interpretation and meaning. The use of "including" and "comprising" and variations thereof is meant to encompass the items listed thereafter and equivalents thereof as well as additional items and equivalents thereof.

By way of introduction, aspects discussed herein may relate to apparatus, systems, methods and techniques employing deep learning to generate phase images that may reduce and/or remove the effect of visual artifacts such as dust, water droplets, well borders (e.g., in multiwall plates), image borders, and the like, thereby addressing shortcomings of classic methods associated with such artifacts. For the purposes of this disclosure, "artifact-free" images shall be understood to be images that are substantially free of visual artifacts and/or discontinuities, which absent the application of the disclosed apparatus, systems, methods and techniques, would produce substantial image distortion. As also used herein, "specimen" refers to the contents of a view to be imaged, or "image view", such as a microscope view, where such specimen may include one or more objects, structures, samples, etc. In one embodiment, training set images from artifact-free views of a specimen (e.g., a microscope view) using at least two different focal planes may be obtained to provide at least first and second brightfield images, and an artifact-free phase image of the views can be obtained therefrom. Thereafter, the at least first and second artifact-free brightfield images can be modified by simulating the presence of visual artifacts or other types of challenges known to be present in brightfield microscopy images. The modified brightfield images, together with the artifact-free phase image (e.g., derived from the unmodified brightfield images) are provided as input to a machine learning model as a training set. The machine learning model may generate an output phase image based on matched images of the training set based on the phase equation and one or more model parameters. In such an embodiment, the parameters of the machine learning model are adjusted to compensate for the simulated, artifact-induced brightfield images in view of the artifact-free phase image (based on the artifact-free brightfield images). Following training, when presented with sample brightfield images containing actual artifacts, the disclosed apparatus, methods, and systems are able to utilize the trained machine learning model to compute a phase image of a corresponding view that compensates for the artifacts.

In some embodiments, a machine learning model (e.g., a neural network) may be trained to generate phase images from a pair of brightfield images of a specimen taken at different focal planes. The model may be trained to obviate common issues that can render classically generated phase images unusable in part. A training data set may be constructed through selection of a relatively clean set of matched images, which may be selected to provide examples image views of the specimen or (sub)regions thereof that avoid visual artifacts and other issues. For example, a model may be trained to operate on training images (e.g., from at least two different focal planes) of a cutout region within a full brightfield image, which may allow the model to learn to reduce and/or remove the impact of image borders. The training data set may be expanded by taking matched image sets and modifying the images to simulate the presence of visual artifacts or other challenges incumbent on the practicalities of brightfield microscopy. Because the visual artifacts are simulated, the output of the model can still be evaluated against a known ground truth example. This process may result in the trained model learning to compensate for visual artifacts, reducing their impact on the generated phase image. Once trained, the model may be employed to generate improved phase images from brightfield images/image views that may contain visual artifacts and/or discontinuities.

Model training may be supervised learning, unsupervised learning, and/or a hybrid learning approach. In supervised learning, each matched image set in the training data set may include a corresponding ground truth phase image (e.g., a phase image derived from unmodified, artifact-free brightfield images). Output of a machine learning model during training may be compared to the ground truth phase image, and the model parameters may be adjusted appropriately. In unsupervised learning, the output of the machine learning model during training may be compared to an expected ground truth phase image calculated by applying the phase equation (and/or additional enhancements) to the unmodified, artifact-free brightfield images. In some embodiments, a hybrid approach may be used as well, employing aspects of both supervised and unsupervised learning to obtain improved model training.

According to some aspects, a supervised learning system and/or method may use classically reconstructed phase images from artifact-free image views of the specimen or portions thereof, selected away from image borders, and clean from visual artifacts, as ground truth for training the machine learning algorithm. A deep artificial neural network model may be trained to reproduce the phase image reconstruction. To account for the disturbances and artifacts described herein, image augmentation tools may be employed to simulate those artifacts on the images of the artifact-free training data set (and/or corresponding ground truth phase images) to allow the artificial neural network to learn different ways to deal with those (simulated) artifacts. For example, darkened areas in the artifact-free training data and/or ground truth phase images may be created to emulate the effect of dust particles or liquid droplets, where such artifact creation/simulation may account for focal planes of corresponding brightfield images and the effect, if any, on the artifact being simulated. The network may be trained to ignore the contribution from darkening. Additionally and/or alternatively, some areas of the artifact-free training images may be "blacked out" to simulate the effect of image borders or well borders. In this case, the network may be trained to keep these areas as blacked out areas, and not to influence the phase signal in near-by image regions. These augmentation tools/techniques may greatly improve the success of the supervised methods. In some embodiments, the disclosed apparatus, methods and systems may include projecting the simulated visual artifact to the a different brightfield image based on a difference between a first focal plane associated with a first brightfield image and a second focal plane associated with a second focal plane An unsupervised learning method, according to some aspects, might not rely on the classically reconstructed phase images. Instead, the unsupervised method may rely primarily on phase equations directly as loss functions when training the artificial neural network model. This approach may not require the use of image augmentation tools/ techniques in the same manner, and is able to account for the artifacts and image quality problems identified earlier. However, since the unsupervised approach largely relies on the phase equation (and related enhancements), it may reconstruct additional details in the phase images that could suffer from similar problems in classical reconstructions. Accordingly, in some unsupervised embodiments, brightfield images are provided as input to the machine learning model, and random weights may be used to compute a phase image. The phase equation may be used to calculate the loss and adjust the weights. This process can be repeated until a phase image is obtained that yields a predetermined or otherwise desired loss.

Hybrid learning apparatus, systems and/or methods, according to some aspects, may use both supervised and unsupervised methods to train the model to perform the reconstructions. Applying these learning methods to train the machine learning model may provide a model that is able to remove and/or reduce the impact of visual artifacts automatically, without the need for manual parameter tuning associated with classical adjustments.

The process of generating phase images using a set of brightfield microscopic images measured at different focal planes is a known method. While it works well in some use-cases, this approach does not perform well when faced with common artifacts (e.g., dust particles, well borders), and takes time (i.e. 3-5 seconds) to generate one phase image.

Before discussing these concepts in greater detail, however, several examples of a system and/or method comprising a computing device that may be used in implementing and/or otherwise providing various aspects of the disclosure will first be discussed with respect to FIG. 1.

FIG. 1 illustrates one example of a computing device 101 that may be used to implement one or more illustrative aspects discussed herein. For example, computing device 101 may, in some embodiments, implement one or more aspects of the disclosure by reading and/or executing instructions and performing one or more actions based on the instructions. In some embodiments, computing device 101 may represent, be incorporated in, and/or include various devices such as a desktop computer, a computer server, a mobile device (e.g., a laptop computer, a tablet computer, a smart phone, any other types of mobile computing devices, and the like), and/or any other type of data processing device.

Computing device 101 may, in some embodiments, operate in a standalone environment. In others, computing device 101 may operate in a networked environment. As shown in FIG. 1, various network nodes 101, 105, 107, and 109 may be interconnected via a network 103, such as the Internet. Other networks may also or alternatively be used, including private intranets, corporate networks, LANs, wireless networks, personal networks (PAN), and the like. Network 103 is for illustration purposes and may be replaced with fewer or additional computer networks. A local area network (LAN) may have one or more of any known LAN topology and may use one or more of a variety of different protocols, such as Ethernet. Devices 101, 105, 107, 109 and other devices (not shown) may be connected to one or more of the networks via twisted pair wires, coaxial cable, fiber optics, radio waves or other communication media.

As seen in FIG. 1, computing device 101 may include a processor 111, RAM 113, ROM 115, network interface 117, input/output interfaces 119 (e.g., keyboard, mouse, display, printer, etc.), and memory 121. Processor 111 may include one or more computer processing units (CPUs), graphical processing units (GPUs), and/or other processing units such as a processor adapted to perform computations associated with machine learning. I/O 119 may include a variety of interface units and drives for reading, writing, displaying, and/or printing data or files. I/O 119 may be coupled with a display such as display 120. Memory 121 may store software for configuring computing device 101 into a special purpose computing device to perform one or more of the various functions discussed herein. Memory 121 may store operating system software 123 for controlling overall operation of computing device 101, control logic 125 for instructing computing device 101 to perform aspects discussed herein, machine learning software 127, training set data 129, and other applications 129. Control logic 125 may be incorporated in and/or may be a part of machine learning software 127. In other embodiments, computing device 101 may include two or more of any and/or all of these components (e.g., two or more processors, two or more memories, etc.) and/or other components and/or subsystems not illustrated here.

Devices 105, 107, 109 may have similar or different architecture as described with respect to computing device 101. Those of skill in the art will appreciate that the functionality of computing device 101 (or device 105, 107, 109) as described herein may be spread across multiple data processing devices, for example, to distribute processing load across multiple computers, to segregate transactions based on geographic location, user access level, quality of service (QoS), etc. For example, devices 101, 105, 107, 109, and others may operate in concert to provide parallel computing features in support of the operation of control logic 125 and/or software 127.

One or more aspects discussed herein may be embodied in computer-usable or readable data and/or computer-executable instructions, such as in one or more program modules, executed by one or more computers or other devices as described herein. Generally, program modules include routines, programs, objects, components, data structures, etc. that perform particular tasks or implement particular abstract data types when executed by a processor in a computer or other device. The modules may be written in a source code programming language that is subsequently compiled for execution, or may be written in a scripting language such as (but not limited to) Python or R. The computer executable instructions may be stored on a computer readable medium such as a hard disk, optical disk, removable storage media, solid state memory, RAM, etc. As will be appreciated by one of skill in the art, the functionality of the program modules may be combined or distributed as desired in various embodiments. In addition, the functionality may be embodied in whole or in part in firmware or hardware equivalents such as integrated circuits, field programmable gate arrays (FPGA), and the like. Particular data structures may be used to more effectively implement one or more aspects discussed herein, and such data structures are contemplated within the scope of computer executable instructions and computer-usable data described herein. Various aspects discussed herein may be embodied as a method, a computing device, a data processing system, or a computer program product.

Having discussed several examples of computing devices which may be used to implement some aspects as discussed further below, discussion will now turn to a process for training a machine learning model to generate brightfield phase images.

Figure 2:
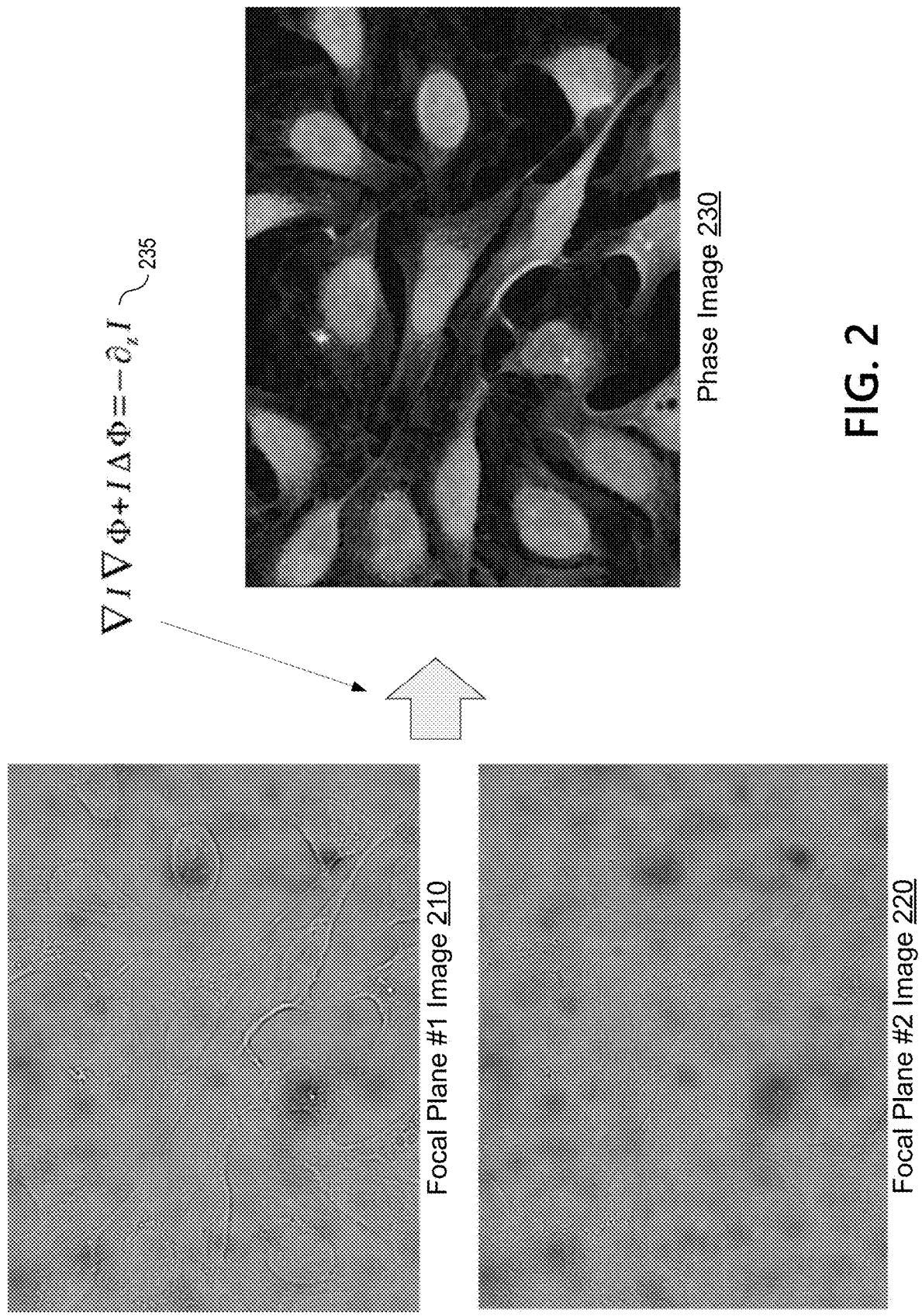
FIG. 2 illustrates example generation of a brightfield phase image, according to some aspects.

FIG. 2 shows an example of the generation of a brightfield phase image from two input brightfield images. A first image 210 and a second image 220 may be images captured from a brightfield microscope using first and second focal planes, respectively. For example, a specimen having a sample containing cells and water may be prepared in a well of a sample plate and placed appropriately for imaging by the microscope. A first image 210 may be an image captured of a view of at least a portion of the specimen at a first focal plane, while a second image 220 may be a corresponding image of the same view of the specimen captured at a second focal plane. Applying the principles of brightfield phase imaging, the first image 210 and the second image 220 may be processed to generate a phase image 230 based on the phase equation 235. This process may leverage the different refraction indexes of the known sample media (e.g., water at n=1.33) and the sample (e.g., cells at n=1.35-1.38) to generate an image that isolates the sample from the background through visual contrast. Application of the phase equation to the images at different focal planes is based on recognizing that a cell operates similarly to a lens, condensing light that passes through the cell as it travels from one layer to the next. Conservation laws of light govern how light moves from one place to another without loss of photons. Applying the phase equation may translate density information from the first and second focal planes to generate the phase image ($\Phi$).

Strict application of the phase equation to input brightfield images may generate phase images that have unusable portions due to the presence of visual artifacts such as dust or well borders, among others, as the present techniques are not limited to these or other examples of artifacts and may be extended to other visual artifacts and/or discontinuities in an image. Classical approaches have developed various tuning enhancements to apply to phase images generated using the phase equation, but often they require manual tuning and application. Corrections applied to the resulting phase image violate the phase equation, but can reduce the impact of visual artifacts that are outliers in terms of refractive index.

Figure 3A:
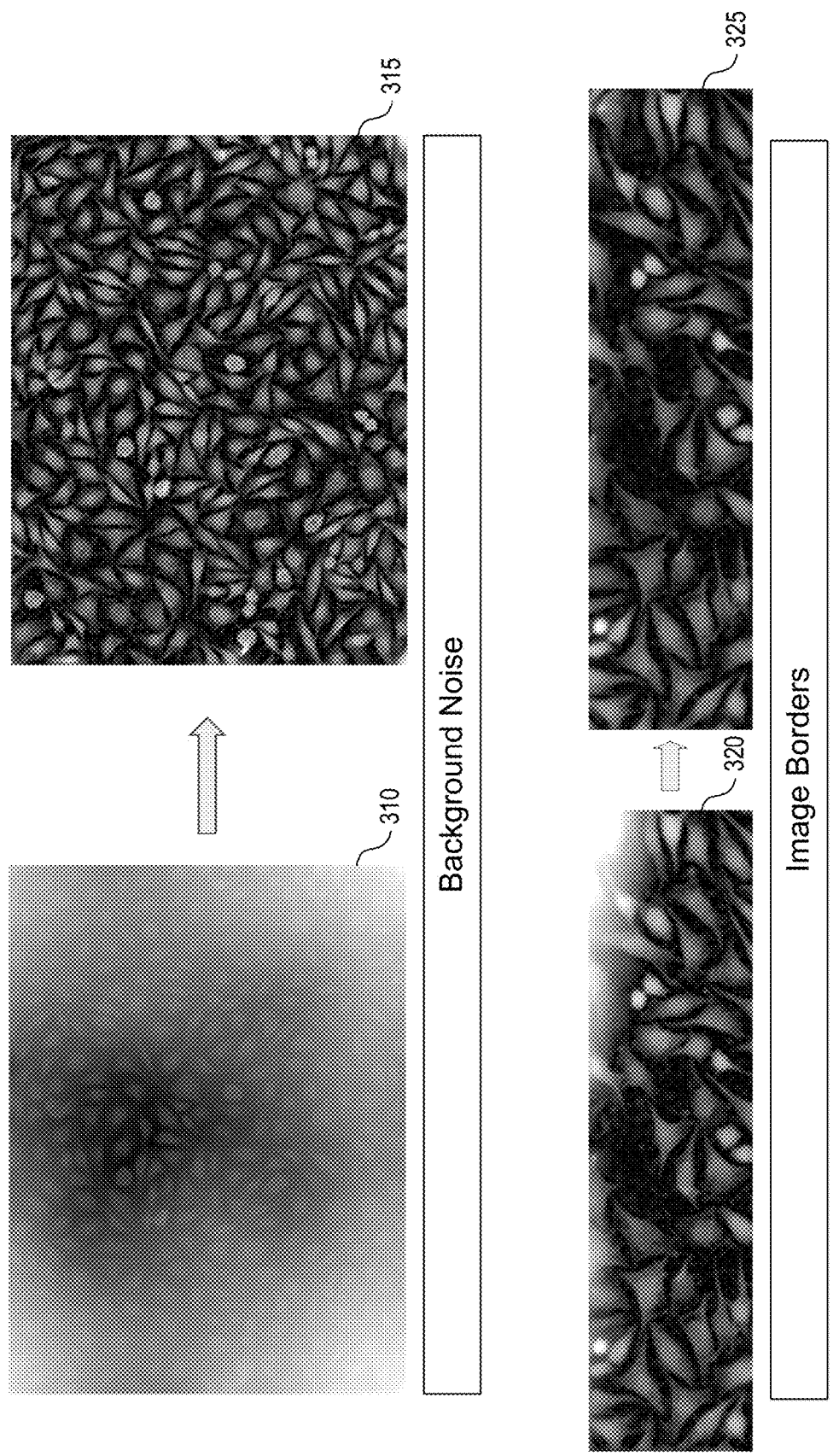
FIGS. 3A-3C illustrate example visual artifacts that may present complications in generated brightfield phase images.
Figure 3B:
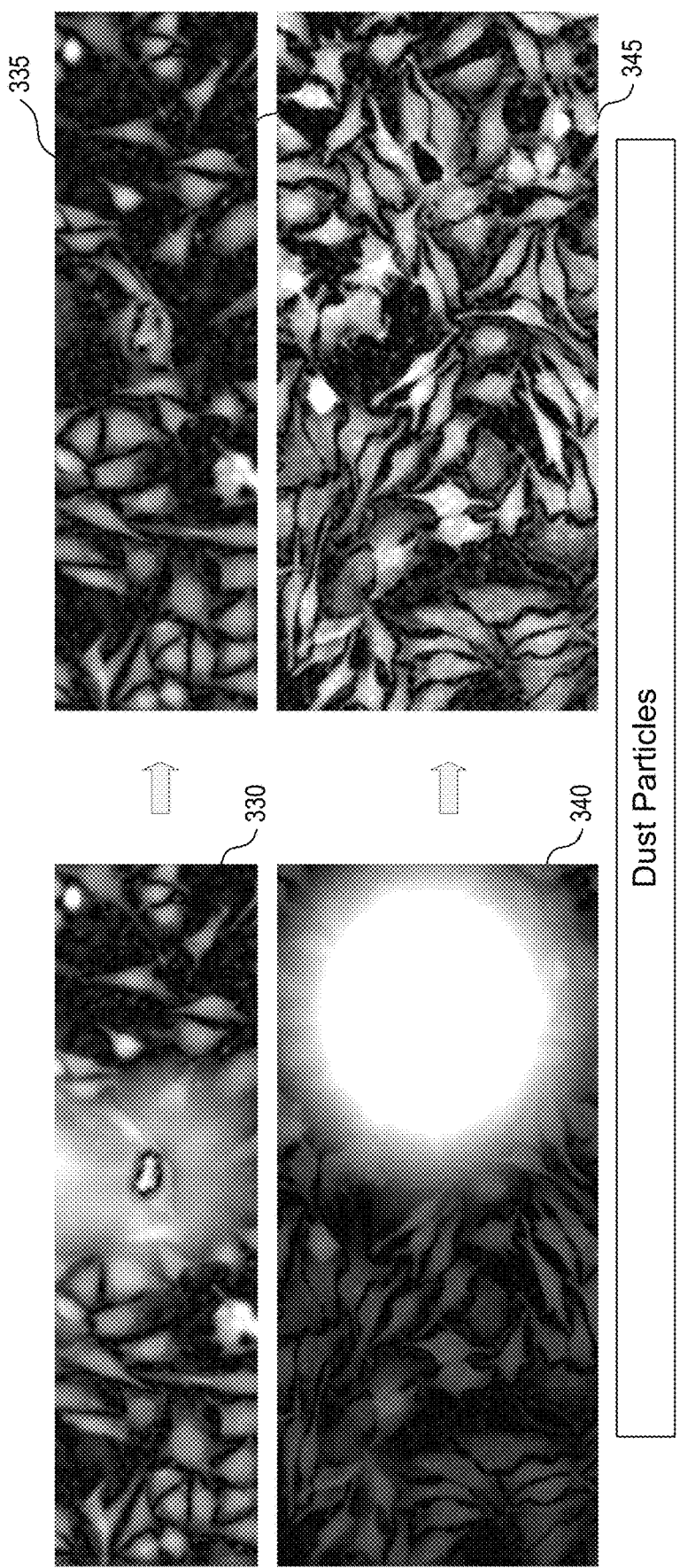
Figure 3C:
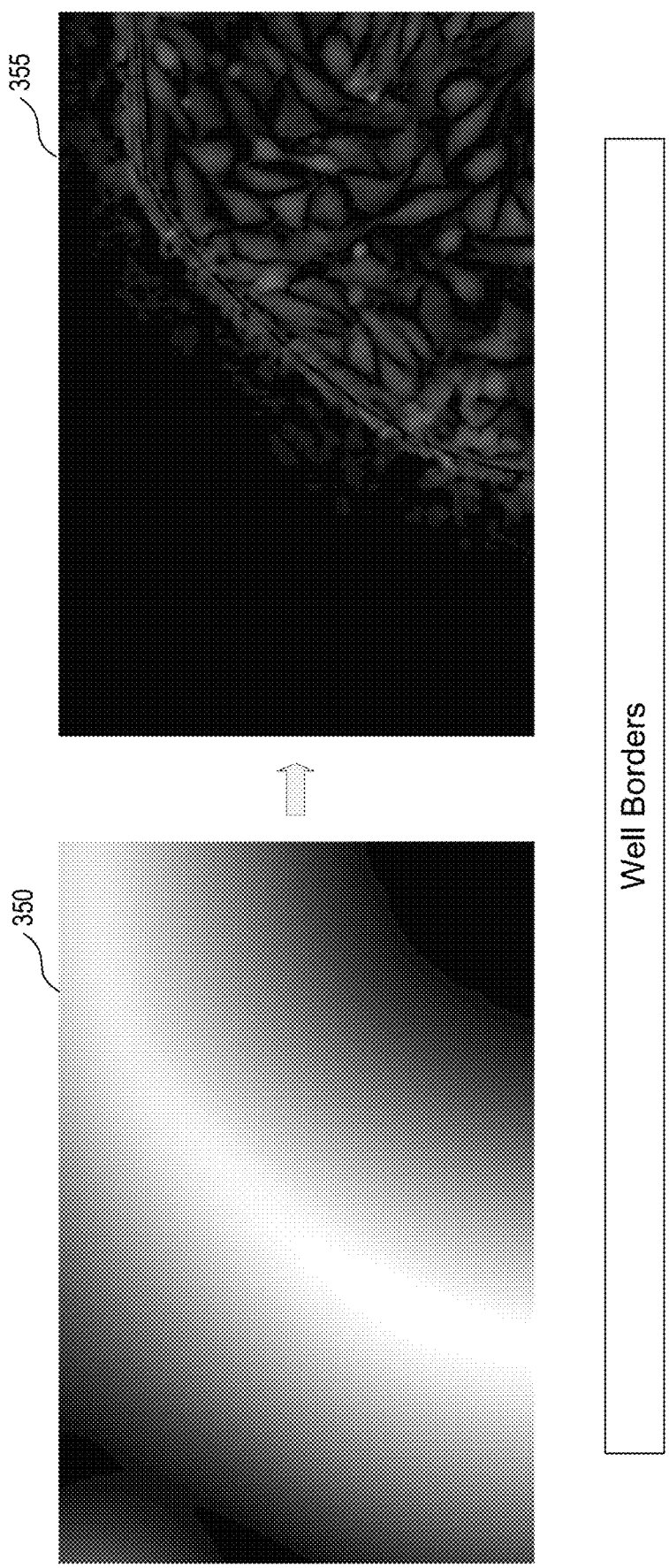

FIGS. 3A-3C illustrate complications in phase imaging, and what a corresponding proper result may look like. In practice, brightfield imaging is subject to imperfections in patterns of illumination, light loss, noise/nuisance, disturbances in light paths, and other visual artifacts.

FIG. 3A illustrates problems associated with background noise and image borders. In exemplary images 310 and 320, providing two views of a particular specimen, visual artifacts and discontinuities in the form of background noise and image borders serve to blur or introduce undesirable contrast in areas near borders of the image view of the specimen. This background glow may result from strict application of the phase equation. In corresponding processed images 315 and 325, a more proper visualization is presented that has adjusted for the contrast problems of images 310 and 320. Classical approaches to compensating for these issues include a background cutoff/sliding cutoff approach. As mentioned, these approaches may violate the phase equation, and indeed may have higher error rates, but result in a generated phase image that is more suitable for observations. While corrections may deviate from the phase equation, they provide improved separation of useful signal from useless signal. Another enhancement may include application of a high pass filter to the generated phase image. However high pass filters may undershoot images and may fall short of satisfactorily solving certain issues. A better approach may be to utilize a sliding parabola as a sort of "razor", interpolating between minima on the phase image to shave the cells of the background glow. However, the sliding parabola approach may require careful tuning and application by an operator.

Similarly, FIG. 3B illustrates problems associated with image views when dust particles are in the image view. Image 330 shows an example resulting phase image derived from classical approaches that gives undue weight to a dust particle, surrounded by a halo of blur and high contrast. Dust particles (such as dust from the air, or a lab coat fiber) included in the specimen image views can yield very bad results, as they are optically absorbent and violate the conservation law phase equation used to generate the contrast phase images. Image 335 shows a processed image corresponding to image 330, where the impact of the dust particle has been reduced. Image 340 shows a similar visual artifact, where a disturbance in the visual path has caused the phase image to black (white) out a section of the image. Image 345 shows a properly adjusted phase image that has removed the effect of the disturbance.

FIG. 3C shows the impact that well borders, such as on multi-well plates, can have on generated phase images. Samples (e.g., biological material, non-biological material, and/or other types of material under investigation) within a specimen may be measured inside small wells of a multiwell plate observed by a microscope, although such example is provided for illustration only and the disclosed methods and systems can be applied to other views of other objects/specimen. Well borders on the plate may operate as a strong absorptive media, optically drowning out useful signal. Unprocessed phase image 350 shows that the well border may absorb light passing through the well border and thus shows on a generated phase image as an area of high contrast, largely unusable for observation. Classical approaches struggle substantially with well borders in images, and such processing approaches may have a long-range damaging effect through a generated phase image (e.g., impact a large visual region). Processed phase image 355 shows an enhanced image, according to some aspects, that removes the effect of the well border, revealing specimen cells that could not be viewed in the native, unprocessed phase image. As described further herein, a significant advantage of using a machine learning approach with simulated visual artifacts to generate phase images may be the trained model's robust treatment of well borders in specimen images.

Figure 4A:
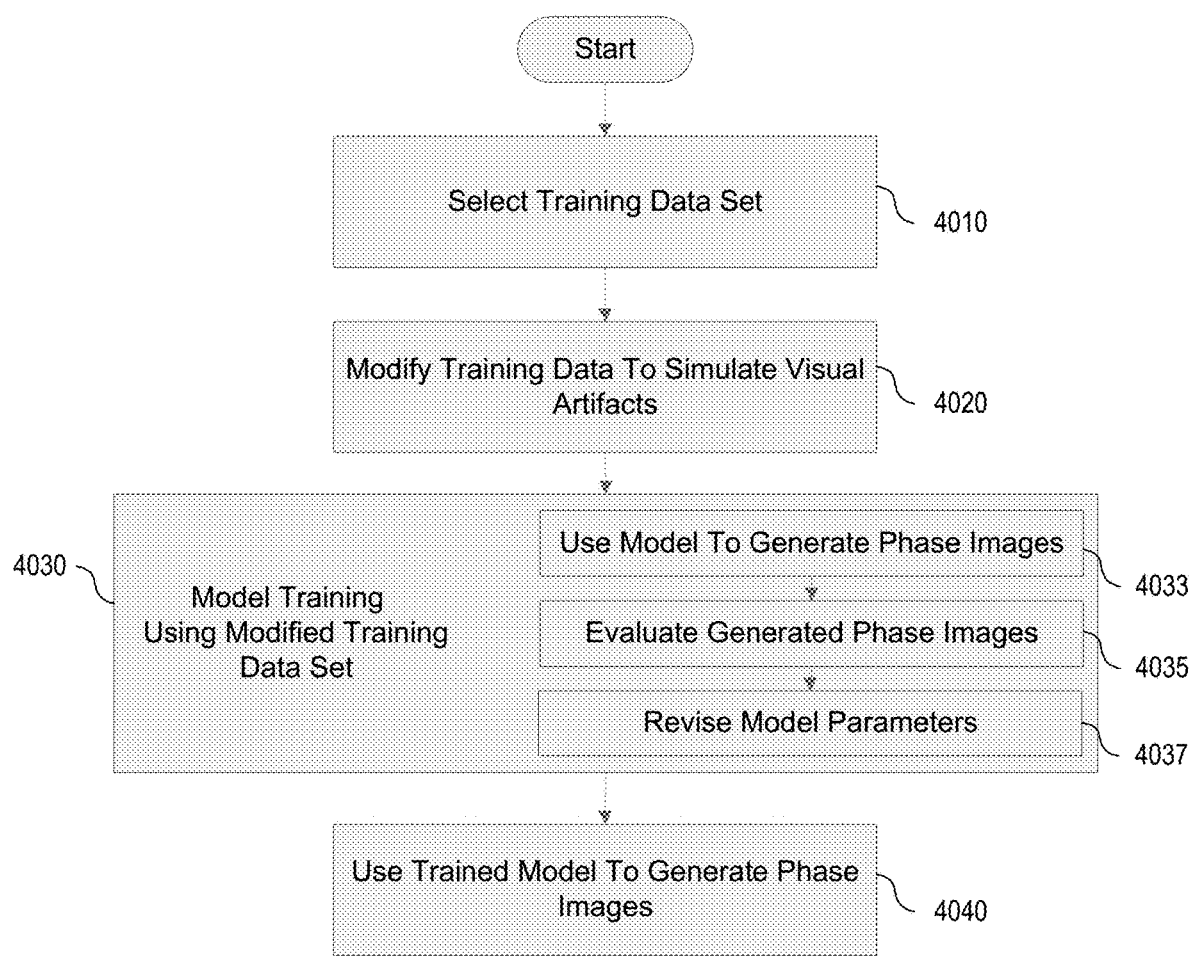
FIG. 4A is a block diagram of an illustrative example of a method for developing training data sets for training a machine learning model to generate phase images, according to one or more aspects.

FIG. 4A illustrates one embodiment of a novel method 4000 for training a machine learning model to generate phase images. Method 4000 may train the machine learning model based on an initial training data set that includes obtaining one or more initial matched sets of brightfield images, each brightfield image in a set taken at a different focal plane. Such initial data set images may comprise views that are substantially free of visual artifacts and/or discontinuities. The training data set may be enhanced by generating additional matched image sets by modifying one or more of the initial matched image training sets (brightfield images) to simulate visual artifacts and/or discontinuities that classical approaches may have difficulty classifying when generating a phase image therefrom. The machine learning model may be trained on the simulated visual artifacts and/or discontinuities to improve the generation of phase images even in the presence of such visual artifacts, which include but are not limited to dust, water droplets, borders such as well borders and plate borders, and other visual artifacts and discontinuities that can arise in brightfield imaging (e.g., as discussed with respect to FIGS. 3A-3C). Method 4000 may be implemented by any suitable computing device (such as computing device 101 of FIG. 1), embodied in computer-readable media, and/or embodied in a suitably configured system. The machine learning model may be an artificial neural network employing deep learning techniques, such as a convolutional neural networks. A deep neural network may be a neural network that includes one or more hidden layers beyond its input and output layers. Many types of artificial neural networks are suitable for generating phase images based on input brightfield images, and aspects described herein may apply equally regardless of the particular neural network structures employed by the machine learning model. As will be understood in the art, candidate phase images generated by the machine learning module may be evaluated using a supervised learning, unsupervised learning, and/or hybrid learning approach, and the parameters of the machine learning model may be adjusted based on the evaluation to improve accuracy of the machine learning model.

At 4010, a computing system implementing method 4000 may select an initial training data set comprising one or more matched sets of images. Each matched set of images in the initial training data set may comprise two or more images of a specimen viewed at different focal planes. For example, a matched set of images may comprise a first brightfield image of a specimen corresponding to a view at a first focal plane and a second brightfield image of the same specimen corresponding to a view at a second focal plane. The initial training data set may be selected to generally comprise matched sets of images that are substantially free from significant visual artifacts and/or discontinuities. For example, the training data set may comprise examples selected to substantially avoid dust particles or well boundaries of a multiwell plate. For supervised learning applications, the training data set may comprise corresponding phase images generated based on the substantially artifact-free matched sets of images. The corresponding phase images may be generated using classical approaches, such as through applying the phase equation to the first and second brightfield images. The phase images may be further enhanced with corrections, such as through application of a sliding parabola correction to reduce background glow/noise.

At 4020, the computing system may enhance the training data set by generating additional matched sets of images by modifying the initial matched sets of images to simulate visual artifacts.

At 4030, the system may train the machine learning model on the enhanced training data set, including the initial "artifact-free" images and the modified images. During training, at 4033, the machine learning model may generate candidate phase images from matched sets of brightfield images in the training data set. In an example embodiment having two brightfield images, a first brightfield image at a first focal plane and a corresponding second brightfield image at a second focal plane of a matched set of images may be input to the machine learning model. In some implementations, where more than two focal planes are captured in a matched set of images, the input may comprise each of the brightfield images at the different focal planes. In the example embodiment described herein, the machine learning model may output a candidate phase image generated based on the first and second brightfield image of the matched set. At 4035, the generated candidate phase images may be evaluated using a supervised learning, unsupervised learning, and/or hybrid learning approach as described below. And at 4037, the parameters of the machine learning model may be adjusted based on the evaluation to improve accuracy of the machine learning model.

Figure 5:
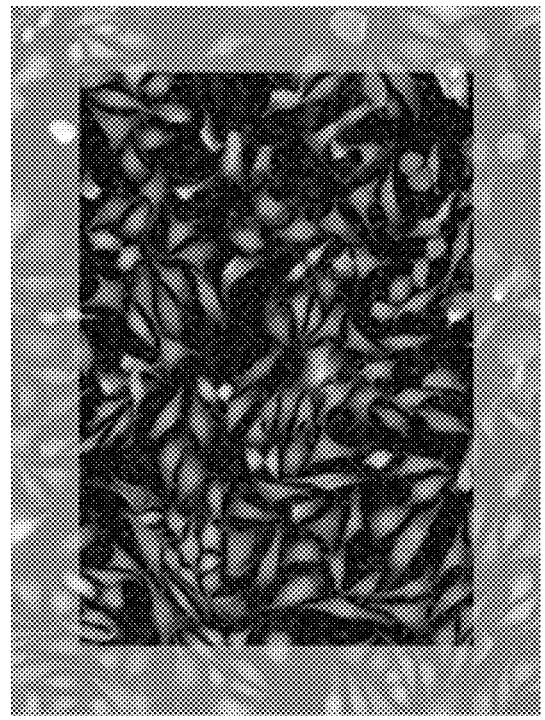
FIG. 5 illustrates an exemplary matched image set for use in training the machine learning model, according to some aspects.
Figure 5:
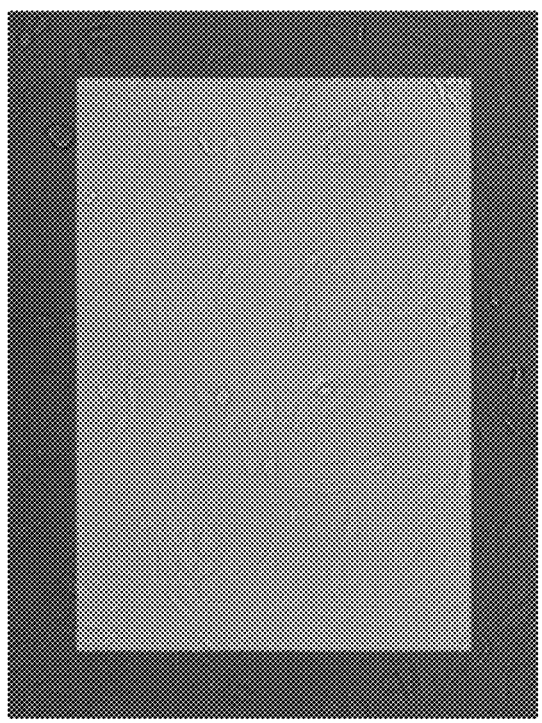
Figure 5:
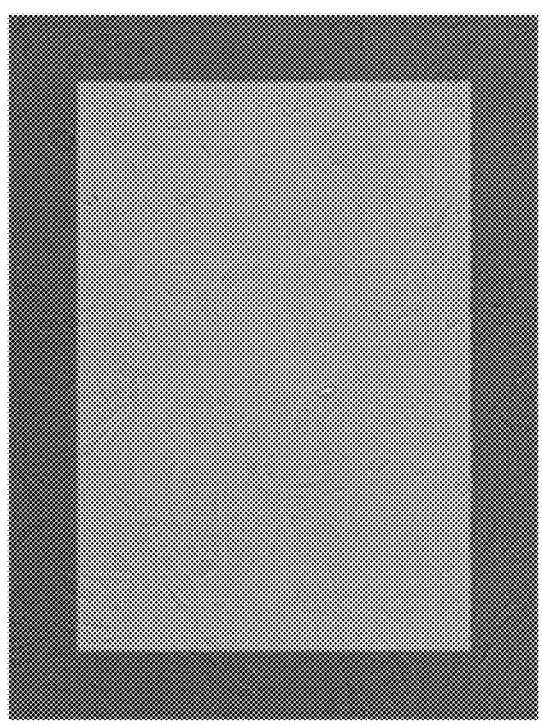

In a supervised learning approach, according to the aforementioned example, which may use the matched set of images illustrated in FIG. 5, a candidate phase image generated by the model and corresponding to a matched set of images from the training data set may be compared to a corresponding ground truth phase image of the training data set (e.g., the phase image generated by classical methods from the substantially artifact-free brightfield image data set(s)), corresponding to the first and second brightfield image. Differences between the ground truth phase image and the candidate phase image generated by the machine learning model may be used to train the model further. That is, parameters of the model may be adjusted based on the differences to adjust and/or improve output of the machine learning model.

In an unsupervised learning approach, the machine learning model generated candidate phase images may be evaluated using a phase equation, along with corrections if desired. That is, the generated (by the model) candidate phase image from a set or plurality of brightfield images may have its error rate evaluated against the optical laws at play in the multiple focal planes of the brightfield images. For example, the phase equation may be used as a loss function, with the candidate phase image and corresponding brightfield images as inputs, in training the machine learning model and the model may be trained to minimize the loss function when generating candidate phase images. Aspects may optimize for minimum loss by performing small random changes to the neural network weights each time the model passes through a training cycle, and the obtained loss may be observed towards the end of each cycle. The obtained loss may be observed over many cycles to evaluate the performance of the best saved model.

In a hybrid learning approach, aspects of both supervised and unsupervised learning may be employed. For example, the machine learning model generated candidate phase images for a matched set of images could be evaluated against a corresponding ground truth phase image while also taking into account error rate relative to the phase equation. Some model parameters might be better adjusted based on the supervised learning, while other model parameters may be better informed based on the unsupervised learning. The supervised and unsupervised approaches may use the same or different data sets. For example, a first training data set may support supervised learning through sets of brightfield images and ground truth phase images, while a second training data set may omit the ground truth phase images.

At step 4040, the trained model may be used to generate phase images from actual data. Data received from a brightfield image source, such as live sets of brightfield images, may be fed into the model to generate phase images that can be provided to a researcher to assist in observation.

Figure 4B:
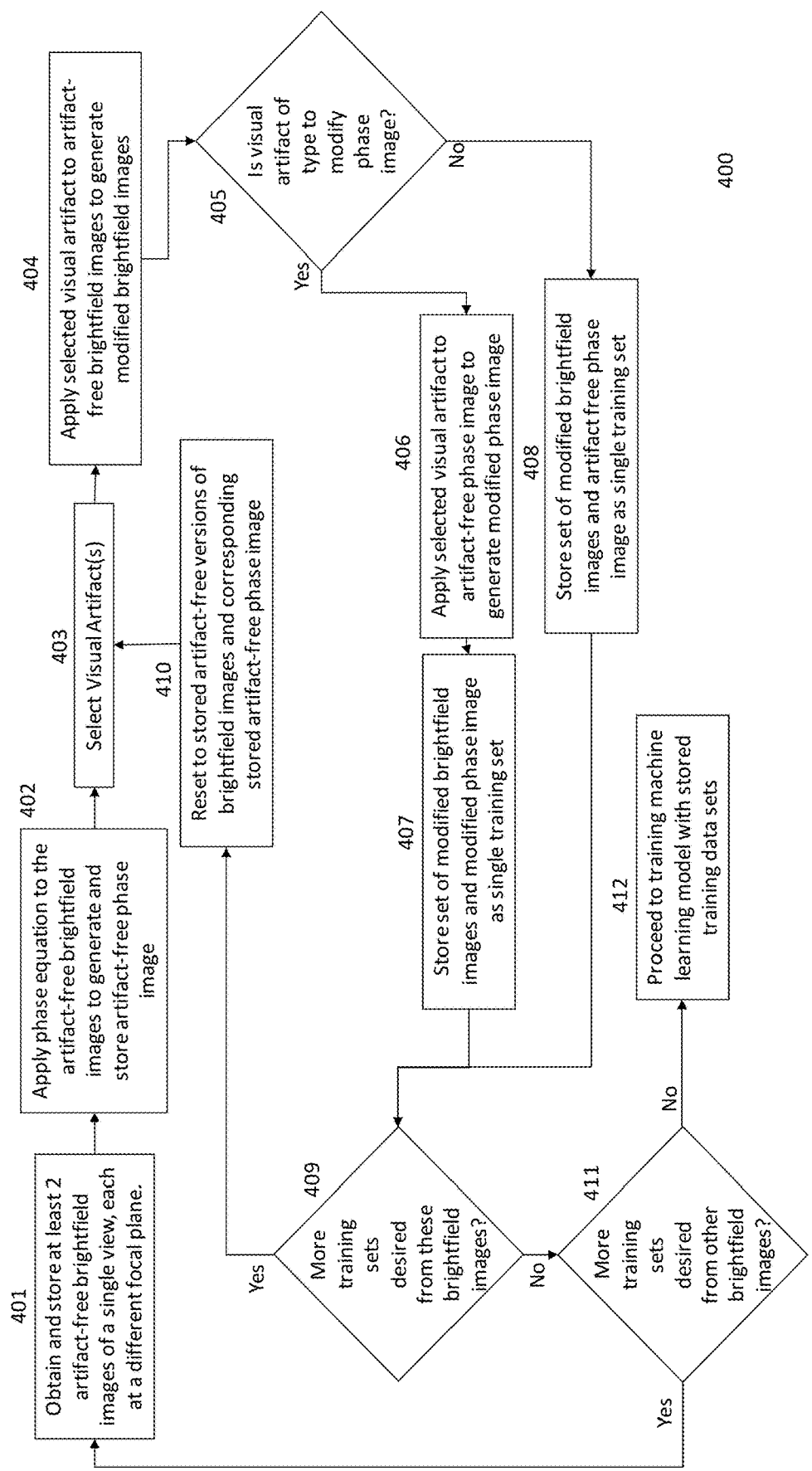
FIG. 4B is a block diagram of an illustrative example of a method for developing training data sets for training a machine learning model to generate phase images, according to one or more aspects.

FIG. 4B illustrates one method 400 for generating training data sets for training of a machine learning model to generate phase images as disclosed by the apparatus, methods and systems described herein. In the FIG. 4B example, the view is a microscope view. Method 400 may implement aspects of method 4000 (FIG. 4A). Method 400 may train the machine learning model based on a training data set that includes matched sets of at least two brightfield images of a microscope view, with each brightfield image taken using a different focal plane. As shown in FIG. 4B, an initial training data set may be constructed based on selecting examples of matched images or image views that are substantially and/or relatively free from visual artifacts or discontinuities. The initial training data set may be enhanced by generating additional matched sets of (modified brightfield) images from the initial training data set images and simulating visual artifacts and/or discontinuities on the initial training data set images that classical methods may have difficulty classifying or otherwise processing. Modification of such brightfield images may be based on the different focal planes associated with the different brightfield images, and the potentially different visual effects of the artifact/discontinuity at the different focal planes. In embodiments of certain learning schemes, the disclosed methods and systems may also include modifying the "ground truth" phase image (generated from the substantially artifact-free brightfield images) with corresponding visual artifacts and/or discontinuities as made to the brightfield images. The machine learning model may be trained on the simulated visual artifacts to improve the generation of phase images even in the presence of such visual artifacts, which in the illustrated embodiment, may include but are not limited to dust, water droplets, well borders, and other visual artifacts that can arise in brightfield imaging (e.g., as discussed with respect to FIGS. 3A-3C). Method 400 may be implemented by any suitable computing device (such as computing device 101 of FIG. 1), embodied in computer-readable media, and/or embodied in a suitably configured system.

At 401, a computing system implementing method 400 may generate an initial training data set by selecting matched sets of at least two brightfield images, each image of a matched set comprising an image view of a specimen at a different focal plane. For example, in the case of two brightfield images, a first brightfield image would be taken of a specific microscopic view of a specimen at a first focal plane, and a second brightfield image would be taken of the same microscopic view of the same specimen but corresponding to a second focal plane. The images selected in 401 may be substantially "artifact-free," preferably substantially free of any significant and/or undesirable visual artifacts and/or discontinuities. In a supervised learning implementation, at 402, a training phase image may be generated based on a corresponding matched set of (artifact-free, initial training data) brightfield images obtained at 401, by applying the phase equation thereto. The corresponding training phase image ("ground truth phase image") may thus be generated using classical approaches, although other techniques may be used. The corresponding training phase image may be further enhanced with corrections, such as through application of a sliding parabola correction to reduce background glow/noise. The "artifact free" brightfield images and their corresponding "artifact free" phase image can be stored. In unsupervised learning implementations, 402 may be omitted.

At 403, one or more visual artifacts may be selected, and may include any one of more of visual artifacts that are typical of brightfield images for the specimen or sample type within the view, as previously set forth herein. As previously provided, such visual artifacts may include dust, well or plate borders, blacked-out regions, etc., and the present disclosure is not limited to the type of visual artifact that may be selected for simulation as provided herein as such artifacts and/or discontinuities are based on the specimen and its properties. At 404, such one or more selected visual artifacts may be applied in a simulated manner to each of the "artifact-free" brightfield images using known techniques, such as by shifting pixels horizontally and vertically, rotating pixels of the image, adding random background noise (e.g., gaussian noise, salt & pepper noise, Poisson noise, speckle noise, etc.), blurring pixels, generating black-out regions in specified areas to simulate microwell or microplate borders, etc., and/or generating random blackout regions throughout the (previously artifact-free brightfield) image.

At 405, it may be determined whether the visual artifacts should also be applied in a simulated manner to the "artifact-free" phase image that was generated from and corresponds to the "artifact-free" brightfield images. Such decision may be based on the selected artifact(s) and the effects that such artifacts may have on the learning process. For example, microwell plate borders and well borders and other fully-absorbing visual artifacts may be chosen to be replicated in the (artifact-free) phase image to better guide the machine learning. Other artifacts may not be simulated in the phase image.

If it is decided to modify the "artifact-free" phase image with visual artifacts, at 406 a corresponding modified phase image may be generated. The modified brightfield images and the modified phase image comprise a matched set of images and are stored as part of the training data set at 407. Otherwise, where the visual artifact is not applied to the phase image, the "artifact-free" phase image and the modified brightfield images comprise a matched set of images and are stored as part of the training data set at 408. After the modified matched set of images are stored, it may be decided at 409 to create another matched set of images using these same initial images, but with a different artifact. In such instances, the process described herein can repeat at 410, generating a new matched set of images to augment the training data set based on the same "artifact-free" brightfield images and corresponding "artifact-free" phase image 410, but with different artifacts. Additionally and/or alternatively, at step 411, a new set of "artifact-free" brightfield images may be obtained by returning to step 401 and method 400 as shown in FIG. 4 can be repeated to generate modified matched sets of images based on other initial matched sets of brightfield images, and/or other matched sets of training data previously generated. For example, in some implementations rather than "resetting" as shown in 410, the system may select a matched set that has already been modified, and further modify it with another artifact. Once the training data set includes all desired sets of images, the training data set can be provided to train a machine learning model at 412 to generate phase images for use by researchers and other users.

FIG. 5 depicts an illustrative matched set of images 500 of an exemplary training data set where the number of brightfield images obtained (see FIG. 4B, 401) is two. Matched set of images 500 may comprise a first brightfield image 510 of a specimen taken at a first focal plane and a second brightfield image 520 of the specimen taken at a second focal plane. Phase image 530 may be generated by applying the phase equation to images 510 and 520, along with suitable corrections such as a sliding parabola correction.

Example images 510, 520, and 530 may be substantially free of undesired artifacts, e.g., having image borders removed such that the machine learning model is not trained on aberrant results near an image border. For example, image data within a certain pixel range of the image border may be removed from training data set images 510, 520, and 530. In some embodiments, the machine learning model may consider data from images 510 and 520 to better inform training to arrive at phase image 530 as a ground truth. Though the model is aiming to generate the reduced region of phase image 530, it may consider additional data from outside that region in images 510 and 520 to better predict the content within the reduced region, in some implementations.

Figure 6:
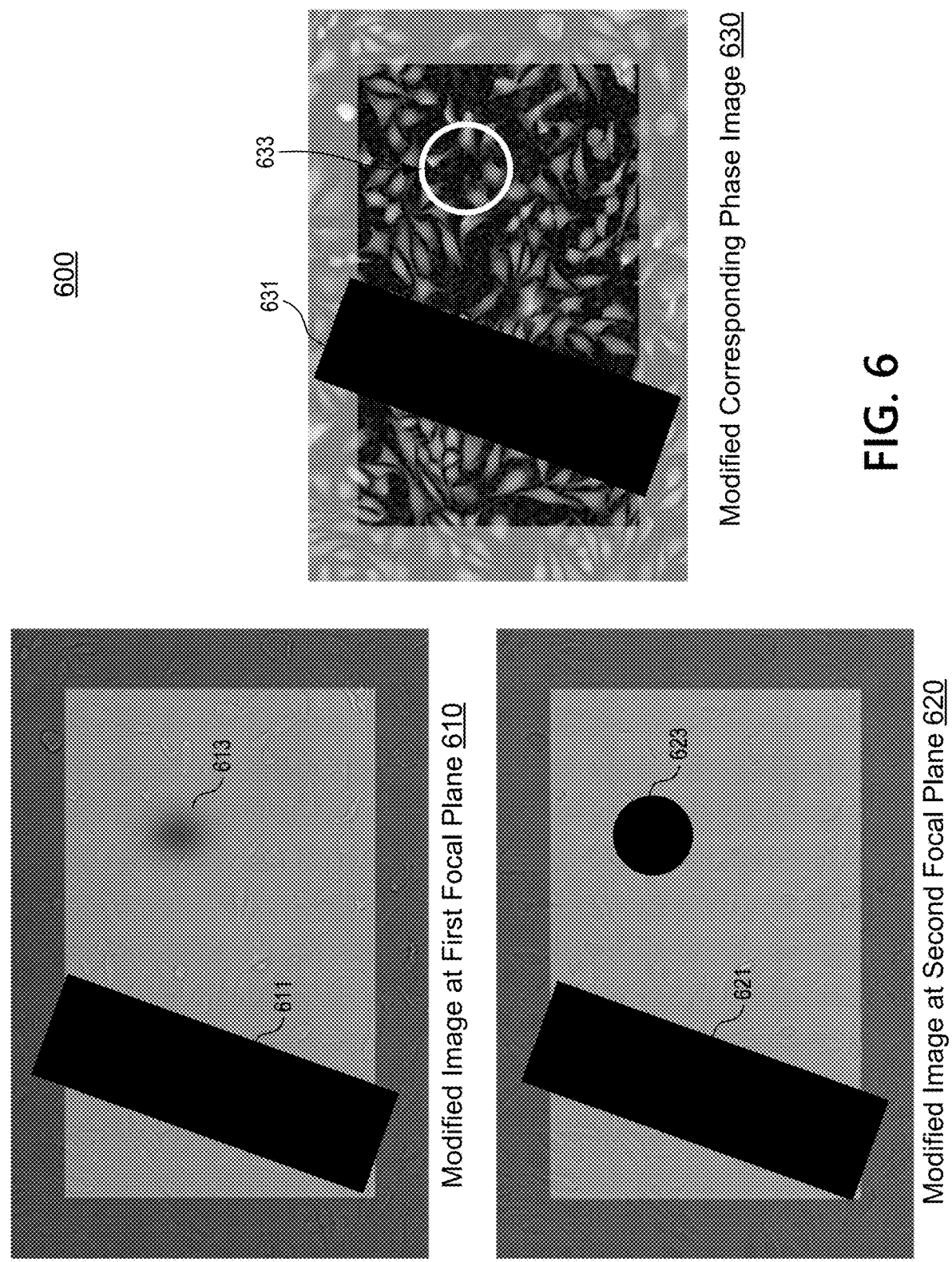
FIG. 6 illustrates an exemplary modified matched image set for use in training the machine learning model, according to some aspects.
Figure 7:
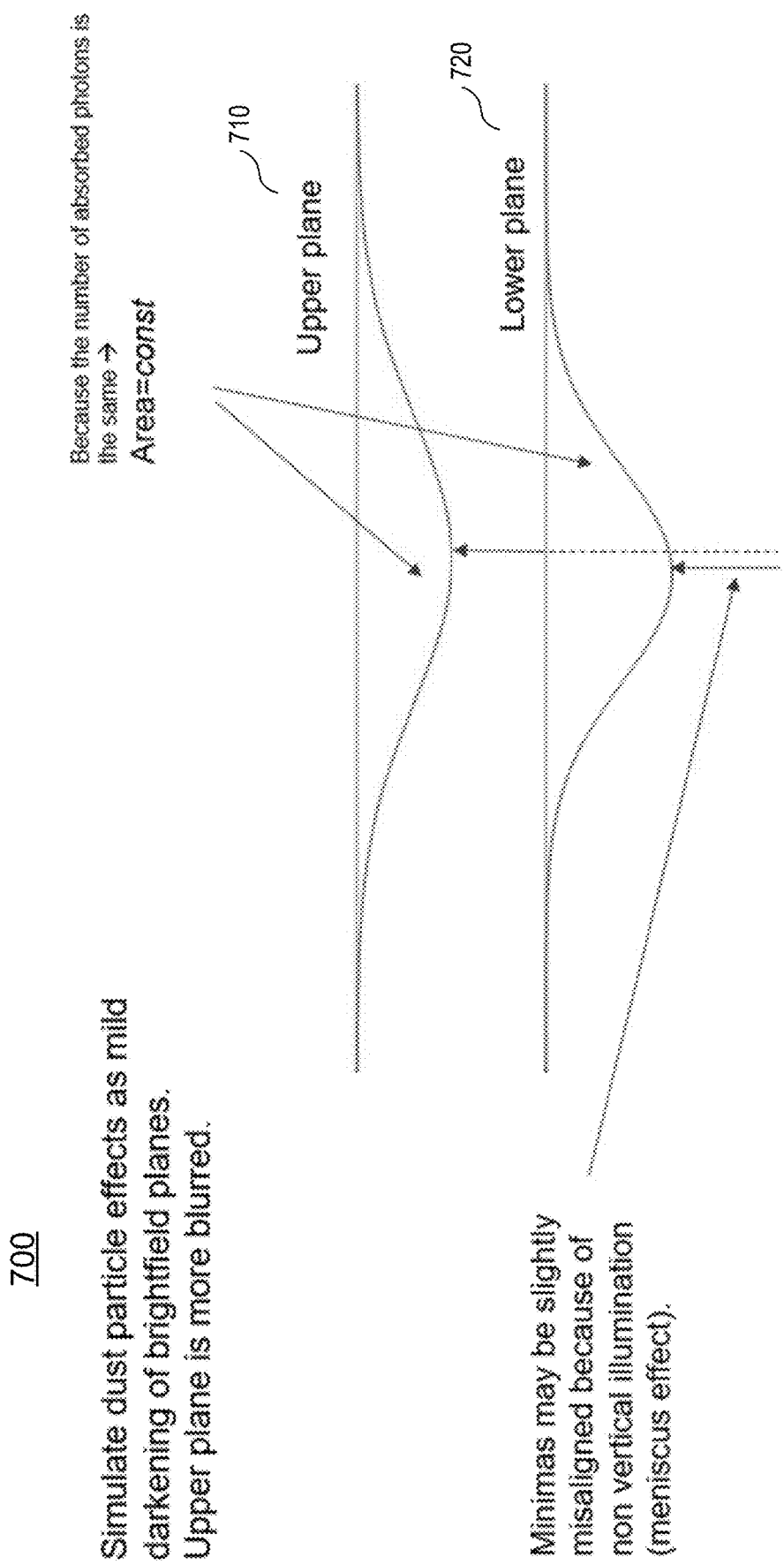
FIG. 7 illustrates optical principles associated with simulating a visual artifact, according to some aspects.

FIG. 6 depicts and illustrative modified matched set of images 600 of an exemplary training data set comprising two brightfield images. A first modified brightfield image at a first focal plane 610 may be modified to include simulated well border 611 and simulated dust particle 613. These simulated artifacts may be projected to a corresponding second brightfield image corresponding to a second focal plane, and a corresponding ground truth phase image. For example, modified second brightfield image 620 is modified to include simulated well border 621, which may be substantially the same as simulated well border 611 due to the nature of well borders as transcending focal planes of the specimen. But dust particle 613 may be projected to have a larger impact on modified training data set second brightfield image 620 due to the difference in focal planes between first and second brightfield images. For example, using the optical properties associated with dust and a distance between the first focal plane and the second focal plane, the system may calculate that the dust should appear less concentrated and more disperse in the first focal plane 610 as compared to the second focal plane 620 where the dust appears sharper (e.g., deeper and darker). FIG. 7 provides an illustration 700 of the optical principles involved in projecting a simulated artifact from one plane to another. In particular, an upper plane 710 may be more blurred than a lower plane 720 due to how dust particles actually interact with light. Additionally, a meniscus effect may cause the projected dust particle to slightly change location when projected to the second focus level. Accordingly, the disclosed methods and systems include simulating and artifact and/or discontinuity by modifying the artifact-free (e.g., "initial") training data set images based on a selected artifact/discontinuity and the associated visual effect of such selected artifact/discontinuity at the corresponding focal plane.

As provided in FIG. 4B, at 405-408, where appropriate the ground truth phase image corresponding to the training data set may be modified to project the desired impact of the simulated visual artifact. For example, the system may generate modified training data set phase image 630 to include simulated well border 631 in substantially the same form as in images 610 and 620. But the visual impact of simulated dust particle 613 may be greatly reduced as shown in region 633. Thus, the simulated visual artifacts may be configured to guide the machine learning model to a desirable result, suitably compensating for visual artifacts in a manner that maximizes useful signal and reduces useless signal.

Because the (initial or artifact-free) training data set includes examples selected to avoid visual artifacts and other complications, such as those illustrated in FIG. 5, the machine learning model may be trained to accurately generate phase images on relatively clean input data. However, according to aspects described herein, modified example matched sets of images, such as those illustrated in FIG. 6, may be employed to train the machine learning model to handle visual artifacts in views of the specimen.

In the disclosed apparatus, systems, and methods, by starting with clean (e.g., substantially artifact-free from undesired artifacts) images/training data, modifications can be made to the matched set of brightfield images while the system still knows a ground truth phase image corresponding to the matched set. Thus, the performance of the machine learning model against the modified examples with simulated visual artifacts can be evaluated based on how accurately the machine learning model is able to arrive at simulated ground truth phase image or the unmodified original ground truth phase image.

As provided herein, for example, a first brightfield image at a first focal plane and a corresponding second brightfield image at a second focal plane of a modified training data set (of the same specimen) may be input to the machine learning model. The machine learning model may output a candidate phase image generated based on the first and second brightfield image of the modified training data set. That is, the candidate phase images generated by the machine learning model may be based on the simulated artifacts. The generated candidate phase images may be evaluated using a supervised learning, unsupervised learning, and/or hybrid learning approach similar to that described above. In particular, the generated candidate phase images may be evaluated against a ground truth phase image corresponding to the modified training data set (whether it also includes simulated visual artifacts, or is unmodified) in a supervised learning approach. In some embodiments, the generated candidate phase image may be evaluated using an unsupervised approach, using the phase equation, applied to the modified brightfield images of the example, as a loss function to guide training of the model. In some embodiments, a hybrid approach may be applied, as discussed above. As stated herein the parameters of the machine learning model may be adjusted based on the evaluation to improve accuracy of the machine learning model.

Once trained, the machine learning model may be used to generate phase images from actual brightfield image data. Data received from a brightfield image source, such as live sets of brightfield images, may be fed into the model to generate phase images that can be provided to a researcher to assist in observation. The model, having been trained on artifact-simulated data during the training stage, may be robust to visual artifacts in the actual data.

Figure 8A:
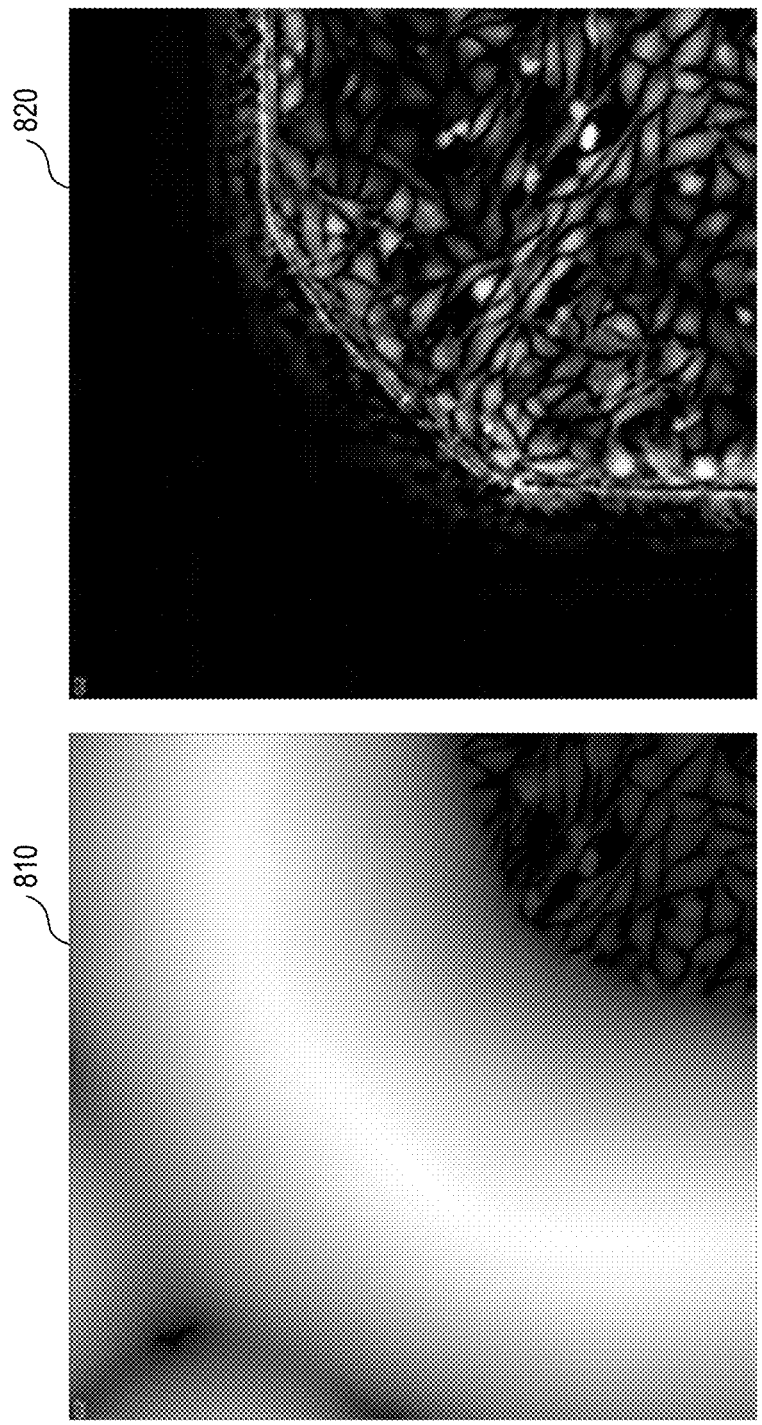
FIGS. 8A-8B illustrate comparative results between classic methods and novel techniques according to one or more aspects described herein.
Figure 8B:
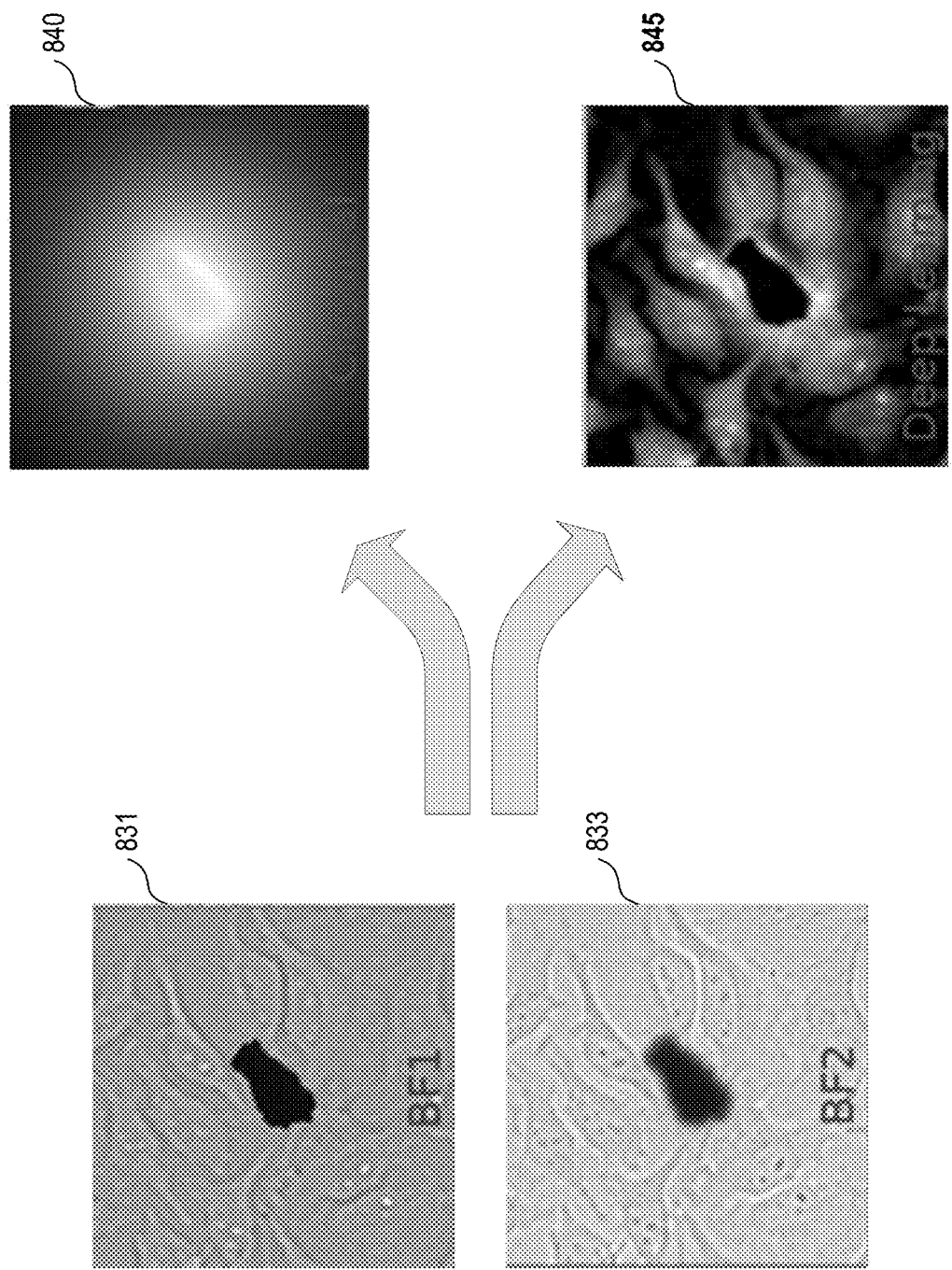

FIGS. 8A and 8B illustrate examples of results from a machine learning model trained according to some aspects described herein in comparison with the results of classical approaches. FIG. 8A illustrates how the classical approach would fail when presented with well borders in image 810. Image 820, generated according to an implementation of some aspects described herein, provides a clear visualization of the well border while still showing cells that are near the well border. As another example, FIG. 8B compares treatment of a dust particle in the brightfield images by an implementation of aspects described herein against classical approaches. First brightfield image 831 and second brightfield image 833 include a dust particle that is highly optically absorptive compared to the cells and water of the specimen. In the classical approach, resulting phase image 840 is practically unusable due to useless signal caused by the dust particle. In contrast, image 845 (generated by an implementation of some aspects described herein) minimizes the useless signal introduced by the dust particle and preserves useful signal of the cells around the dust particle.

As discussed above, aspects described herein relate to a process for training a machine learning model to generate phase images from brightfield images. Aspects described herein may apply equally regardless of the structure of the machine learning model. An exemplary implementation may use a convolutional deep neural network structure for the machine learning model. In particular, one example implementation of a machine learning model that can be used is detailed below. In this implementation, the machine learning model may be implemented based on the TensorFlow library provided by Google. This model may have a "U" shape, progressively scaling down an input image to identify relevant features before scaling back up to the resultant image. U-shaped architectures may proceed through a series of layers that progressively reduce the image until arriving at a single pixel level, then deconvolutions are employed to work back up to a full-scale image.

The U-shaped network may iteratively downscale resolutions of images, such as 4× each step. At each convolution, 1 pixel may correspond to 4 or 16 pixels from prior level. As a result, at each progressive layer the individual pixels include more information. This may facilitate piecewise training of the model and allow the neural network to identify relevant features to consider at various levels of detail. In some implementation, the U-shaped network may be comprised of 3×3 or 4×4 convolutional deep neural network layers of 32 filters. Input images, which may be 256×256 pixels in two planes (e.g. upper plane and lower plane) maybe be progressively filtered down. At each layer, the image may be split into further component images. 256 patches of the images, overlapping, may be fed into the network and processed separately before being tiled back together.

Example Python code using the TensorFlow library to build a convolutional neural network that can be used to implement some aspects described herein is reproduced below:

```
layer1=tf.layers.conv2d(x, 64, 4, 2, 'same',
    activation=tf.nn.leaky_relu)
layer2=tf.layers.conv2d(layer1, 128, 4, 2, 'same',
    activation=tf.nn.leaky_relu)
layer3=tf.layers.batch_normalization(layer2)
layer4=tf.layers.conv2d(layer3, 256, 4, 2, 'same',
    activation=tf.nn.leaky_relu)
layer5=tf.layers.batch_normalization(layer4)
layer6=tf.layers.conv2d(layer5, 512, 4, 2, 'same',
    activation=tf.nn.leaky_relu)
layer7=tf.layers.batch_normalization(layer6)
layer8=tf.layers.conv2d(layer7, 512, 4, 2, 'same',
    activation=tf.nn.leaky_relu)
layer9=tf.layers.batch_normalization(layer8)
layer10=tf.layers.conv2d(layer9, 512, 4, 2, 'same',
    activation=tf.nn.leaky_relu)
layer11=tf.layers.batch_normalization(layer10)
layer12=tf.layers.conv2d(layer11, 512, 4, 2, 'same',
    activation=tf.nn.leaky_relu)
layer13=tf.layers.batch_normalization(layer12)
layer14=tf.layers.conv2d(layer13, 512, 4, 2, 'same',
    activation=tf.nn.leaky_relu)
layer15=tf.layers.batch_normalization(layer14)
layer16=tf.layers.conv2d_transpose(layer15, 512, 4, 2,
    'same', activation=tf.nn.relu)
layer17?=tf.layers.batch_normalization(layer16)
layer18=tf.layers.dropout(layer17, 0.5,
    training=is_training)
layer19=tf.concat((layer12, layer18), axis=3)
layer20=tf.layers.conv2d_transpose(layer19, 512, 4, 2,
    'same', activation=tf.nn.relu)
layer21=tf.layers.batch_normalization(layer20)
layer22=tf.layers.dropout(layer21, 0.5,
    training=is_training)
layer23=tf.concat((layer10, layer22), axis=3)
layer24=tf.layers.conv2d_transpose(layer23, 512, 4, 2,
    'same', activation=tf.nn.relu)
layer25=tf.layers.batch_normalization(layer24)
layer26=tf.layers.dropout(layer25, 0.5,
    training=is_training)
```

```
layer27=tf.concat((layer8, layer26), axis=3)
layer28=tf.layers.conv2d_transpose(layer27, 512, 4, 2,
    'same', activation=tf.nn.relu)
layer29=tf.layers.batch_normalization(layer28)
layer30=tf.concat((layer6, layer29), axis=3)
layer31=tf.layers.conv2d_transpose(layer30, 256, 4, 2,
    'same', activation=tf.nn.relu)
layer32=tf.layers.batch_normalization(layer31)
layer33=tf.concat((layer4, layer32), axis=3)
layer34=tf.layers.conv2d_transpose(layer33, 128, 4, 2,
    'same', activation=tf.nn.relu)
layer35=tf.layers.batch_normalization(layer34)
layer36=tf.concat((layer2, layer35), axis=3)
layer37=tf.layers.conv2d_transpose(layer36, 64, 4, 2,
    'same', activation=tf.nn.relu)
layer38=tf.layers.batch_normalization(layer37)
layer39=tf.concat((layer1, layer38), axis=3)
layer40=tf.layers.conv2d_transpose(layer39, 1, 4, 2,
    'same')
```

Aspects described herein have focused on the training process for the neural network model. The model may be configured to apply corrections to candidate phase images using aspects of classical techniques, such as shift corrections and background glow reduction. The model may be designed to test quality (e.g., as a loss function) using the phase equation. But corrections typically violate the phase equation so the model may be configured suitably, evaluating the accuracy of the generated phase images prior to applying corrections in some implementations. As discussed above with respect to the sample neural network structure, input images may be tiled to facilitate processing, then stitched back together to combine into a final phase image. Aspects of the neural network structure may be tunable. For example, meta parameters (and/or hyper parameters) may be tuned to further improve performance of the machine learning model. As a particular example, the number of filters employed at each layer may be tuned depending on implementation.

Additional neural networks and corrections may be employed to further improve resulting phase images. For example, there may be higher errors on a short resolution scale, in some implementations. High frequency issues may lead to noise in generated phase images. An additional neural network may be employed to denoise the generated phase images. Similarly, blur detection techniques may be employed to further improve the generated phase image.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer implemented method for generating a phase image, the method comprising:
    receiving a training data set comprising one or more matched sets of images, wherein each matched set of images comprises:
        a plurality of brightfield images corresponding to an image view of a specimen, each of the plurality of brightfield images corresponding to a different focal plane; and
        a ground truth phase image generated based on the plurality of brightfield images;
    selecting at least one visual artifact to simulate;
    generating one or more additional matched sets of images by modifying at least one of the one or more matched sets of images of the received training data set to simulate the at least one selected visual artifact in the image view of the specimen, wherein modifying a given matched set of images comprises modifying at least one of the corresponding plurality of brightfield images based on the at least one selected visual artifact;
    adding the one or more additional matched sets of images to the training data set;
    training a machine learning model based on the training data set, wherein training the machine learning model is based on comparing generated output of the machine learning model for a given matched set of images with the corresponding ground truth phase image;
    receiving a first input brightfield image and a second input brightfield image; and
    generating, using the trained machine learning model, a phase image corresponding to the first input brightfield image and the second input brightfield image.

2. The method of claim 1, wherein modifying a given matched set of images to simulate the at least one selected visual artifact comprises:
    modifying a first brightfield image of the given matched set of images based on the at least one selected visual artifact; and
    based on the at least one selected visual artifact and a difference between focal planes of the plurality of brightfield images in the given matched set of images, modifying additional brightfield images in the given matched set of images based on the at least one selected visual artifact.

3. The method of claim 2, wherein modifying the brightfield images comprises at least one of:
    shifting pixels horizontally,
    shifting pixels vertically,
    rotating pixels,
    adding random background noise,
    blurring pixels,
    generating black-out regions in specified areas of the brightfield image,
    generating random blackout regions in the brightfield image, or
    darkening at least one region of the brightfield image.

4. The method of claim 3, wherein adding random background noise comprises adding background noise in a form of at least one of: gaussian noise, salt and pepper noise, Poisson noise, or speckle noise.

5. The method of claim 1, wherein the one or more matched sets of images are selected to avoid plate borders within the image view of the specimen.

6. The method of claim 1, wherein the one or more matched sets of images are selected to avoid imaged visual artifacts within the imaged view of the specimen.

7. The method of claim 1, wherein each ground truth phase image is generated by applying a phase equation to the corresponding plurality of brightfield images.

8. The method of claim 7, wherein each generated ground truth phase image is further processed by applying a sliding parabola correction.

9. The method of claim 1, wherein modifying at least one of the matched sets of images to simulate the at least one selected visual artifact in the image view of the specimen further comprises:
    modifying the corresponding ground truth phase image based on the selected at least one visual artifact.

10. The method of claim 1, wherein the machine learning model comprises a neural network.

11. A computer implemented method for generating a phase image, the method comprising:
receiving a training data set comprising one or more matched sets of images, wherein each matched set of images comprises a plurality of brightfield images corresponding to an image view of a specimen, each brightfield image taken at a different focal plane;
generating one or more additional matched sets of images by modifying at least one of the one or more matched sets of images of the received training data set to simulate at least one visual artifact, wherein modifying a given matched set of images comprises modifying at least one of the corresponding plurality of brightfield images;
adding the one or more additional matched sets of images to the training data set;
training a machine learning model based on the training data set, wherein training the machine learning model is based on evaluating an accuracy of generated output of the machine learning model for a given matched set of images by applying a phase equation to a corresponding plurality of brightfield images;
receiving an input data set comprising at least a first input brightfield image and a second input brightfield image; and
generating, using the trained machine learning model, a result phase image based on the first input brightfield image and the second input brightfield image.

12. The method of claim 11, wherein modifying a given matched set of images to simulate at least one visual artifact comprises:
selecting a simulated visual artifact to apply to a first brightfield image within the corresponding plurality of brightfield images;
visually modifying the first brightfield image to simulate the at least one selected visual artifact based on the focal plane associated with the first brightfield image;
projecting the selected at least one visual artifact to at least one other brightfield image of the corresponding plurality of brightfield images based on a difference between the focal plane associated with the first brightfield image and the focal planes associated with the at least one other brightfield image of the corresponding plurality of brightfield images; and
visually modifying the at least one other brightfield image of the corresponding plurality of brightfield images to simulate the at least one selected visual artifact based on the projecting.

13. The method of claim 11, wherein each matched set of images further comprises a corresponding training phase image, and wherein modifying at least one of the one or more matched sets of images to simulate at least one visual artifact in the image view of the specimen further comprises:
modifying the training phase image based on the at least one visual artifact.

14. The method of claim 11, wherein the one or more matched set of images are selected to avoid plate borders associated within the imaged view of the specimen.

15. The method of claim 11, wherein each matched set of images further comprises a corresponding training phase image, and wherein evaluating the accuracy of generated output of the machine learning model for a given matched set of images further comprises applying a sliding parabola correction to the corresponding training phase image.

16. The method of claim 11, wherein the machine learning model comprises a neural network.

17. An apparatus configured to generate phase images, the apparatus comprising:
data storage storing a training data set comprising one or more matched sets of images, each matched set of images comprising:
a plurality of brightfield images each corresponding to a different focal plane of an imaged view of a specimen; and
a ground truth phase image based on the plurality of brightfield images;
one or more processors; and
memory storing instructions that, when executed by the one or more processors, cause the apparatus to:
modify one or more of the one or more matched sets of images to simulate at least one visual artifact in the image view, wherein modifying a matched set of images comprises modifying at least one of the corresponding plurality of brightfield images based on the at least one visual artifact and the focal plane associated with the brightfield image;
add the modified matched sets of images to the training data set;
train a machine learning model based on the training data set, wherein the training is based on comparing generated output of the machine learning model for a given matched set of images to the corresponding ground truth phase image;
receive an input data set comprising a first input brightfield image and a second input brightfield image; and
generate, using the trained machine learning model, a result phase image based on the first input brightfield image and the second input brightfield image.

18. The apparatus of claim 17, wherein the ground truth phase image associated with the matched set of images is generated based on applying a phase equation to the corresponding plurality of brightfield images.

19. The apparatus of claim 17, wherein the instructions cause the apparatus to modify at least one of the plurality of brightfield images of a given matched set of images by causing the apparatus to:
select at least one simulated visual artifact;
modify a first brightfield image of the corresponding plurality of brightfield images to simulate the at least one selected visual artifact at a first focal plane associated with the first brightfield image;
project the at least one selected visual artifact to at least a second brightfield image within the corresponding plurality of brightfield images based on a difference between the first focal plane and a second focal plane associated with the second brightfield image; and
modify the second brightfield image to simulate the at least one visual artifact at the second focal plane based on the projecting.

20. The apparatus of claim 17, wherein the one or more matched sets of images are selected to avoid visual artifacts within the imaged view of the specimen.

* * * * *